(12) United States Patent
Zünd

(10) Patent No.: US 8,556,427 B2
(45) Date of Patent: Oct. 15, 2013

(54) OPERATING MICROSCOPE SYSTEM

(75) Inventor: René Zünd, Widnau (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 0 days.

(21) Appl. No.: 13/449,818

(22) Filed: Apr. 18, 2012

(65) Prior Publication Data

US 2012/0262671 A1    Oct. 18, 2012

(30) Foreign Application Priority Data

Apr. 18, 2011  (DE) .................. 10 2011 007 607

(51) Int. Cl.
*A61B 3/10*  (2006.01)
*A61B 18/18*  (2006.01)

(52) U.S. Cl.
USPC ........................ 351/221; 359/385; 606/4

(58) Field of Classification Search
USPC ............... 359/368, 385–386, 389; 351/221; 606/4; 362/572, 575
See application file for complete search history.

(56) References Cited

U.S. PATENT DOCUMENTS

| | | | |
|---|---|---|---|
| 4,627,694 A | 12/1986 | Volk | |
| 4,723,842 A | 2/1988 | Twisselmann et al. | |
| 5,009,487 A | 4/1991 | Reiner | |
| 5,865,829 A * | 2/1999 | Kitajima | 606/3 |
| 6,212,006 B1 | 4/2001 | Reiner | |
| 2002/0044256 A1 | 4/2002 | Kirchhuebel | |
| 2002/0118448 A1 | 8/2002 | Kirchhuebel et al. | |
| 2005/0012994 A1 | 1/2005 | Sander | |
| 2008/0204660 A1 | 8/2008 | Obrebski | |
| 2011/0205489 A1 | 8/2011 | Hauger et al. | |

FOREIGN PATENT DOCUMENTS

| | | |
|---|---|---|
| DE | 35 39 009 A1 | 5/1987 |
| DE | 36 15 842 | 11/1987 |
| DE | 36 23 613 | 1/1988 |
| DE | 38 26 069 | 2/1990 |
| DE | 36 88 966 | 4/1994 |
| DE | 200 21 955 | 4/2001 |
| DE | 103 32 603 | 2/2005 |
| DE | 10 2006 038 911 | 2/2008 |
| DE | 10 2007 026 044 | 8/2008 |

(Continued)

OTHER PUBLICATIONS

Horiguchi, M., et al., "New System for Fiberoptic-Free Bimanual Vitreous Surgery", Arch. Ophthalmol., Apr. 2002, vol. 120, pp. 491-494.

(Continued)

*Primary Examiner* — James Phan
(74) *Attorney, Agent, or Firm* — Hodgson Russ LLP

(57) ABSTRACT

An operating microscope system (200) for ophthalmology, particularly vitrectomy, is proposed, which comprises an operating microscope (10) with a microscope illumination (15) and a wide-angle device (20) arranged on the objective side in front of the operating microscope (10), the wide-angle device (20) comprising a wide-angle lens (21) arranged on the object side of the wide-angle device (20) and a prism arrangement (22) for righting the image, arranged on the microscope side of the wide-angle lens (21), wherein the wide-angle device (20) comprises an illuminating unit (25) which is arranged so as to illuminate an object (40) arranged in front of the wide-angle lens (21) through the wide-angle lens (21) by means of an illuminating light (29).

13 Claims, 4 Drawing Sheets

(56) References Cited

FOREIGN PATENT DOCUMENTS

| | | |
|---|---|---|
| DE | 10 2007 026 044 B3 | 8/2008 |
| DE | 10 2009 040 082 | 3/2011 |
| DE | 10 2009 058 792 | 9/2011 |
| EP | 1 326 117 | 12/2004 |
| JP | 2001-108906 A | 4/2001 |
| JP | 2001108906 | 4/2001 |
| WO | 91/15150 | 10/1991 |
| WO | 91/15150 A1 | 10/1991 |

OTHER PUBLICATIONS

Schmidt, J. C., et al., "Bimanualle Membraneextraktion bei schwerer proliferativer diabetischer Vitreoretinopathie mit permanenter Endoillumination", Spektrum Augenheilkd, 2003, vol. 17, No. 4, pp. 177-180, Austria.

* cited by examiner

OPERATING MICROSCOPE SYSTEM

CROSS REFERENCE TO RELATED APPLICATIONS

This application claims priority of German patent application number 10 2011 007 607.7-55 filed Apr. 18, 2011, the entire disclosure of which is incorporated by reference herein.

FIELD OF THE INVENTION

The invention relates to an operating microscope system for ophthalmology, particularly vitrectomy, as well as a wide angle device and an illuminating unit, particularly of such a wide angle device, for an operating microscope system of this kind.

BACKGROUND OF THE INVENTION

Surgical treatment of the vitreous body of the eye by vitreous body surgery is indicated for example in the event of loss of vitreous body during cataract operations, in the event of injuries to the front part of the eye, in paediatric surgery, in retinopathy or in complicated retinal detachments. Different methods are known for this.

The method of choice is Pars Plana Vitrectomy (PPV) which was introduced at the beginning of the 1970s. It is a closed, intraocular microsurgical process in which access to the vitreous space is obtained through the Pars Plana. PPV allows the seamless insertion and removal of surgical instruments through the conjunctiva which is otherwise closed. As a rule, in PPV, a total of 2-3 incisions are required, the diameter of the instruments inserted being 1.0 mm (19 gauge) or 0.9 mm (20 gauge). As a rule, one infusion channel and two working channels are made, enabling the diameter of the individual incisions to be reduced by comparison with a shared access. The effective trauma when a number of small incisions are made is certainly less than when there is one large incision, but the diameter of the individual incisions and the number of incisions should be kept as small as possible.

The standard that has proved successful for illuminating the interior of the eye, as required during PPV, is an endoprobe held in the surgeon's non-dominant hand and introduced into the eye, this endoprobe being connected to an optical fibre. With his dominant hand the surgeon holds the surgical instruments which are then used one-handed to make interventions on the vitreous body and retina. For simpler surgical procedures such as the elimination of a vitreous bleed and the removal of pre-macular membranes, one-handed guidance of the instruments is often practicable. However, for more complex operations inside the eye, two-handed operation is desirable.

In the so-called multiportal illumination system (MIS) developed by Koch et al. (1992) (cf. Augustin, "Augenheilkunde", 3rd Edition, Springer-Verlag Berlin, Heidelberg, 2007), active bimanual vitreous surgery with full wide-angle observation is made possible by the introduction of instruments with a diameter of less than 19 gauge (less than 1.0 mm) into the eye through illuminated cannulas. As a result, no additional illumination, e.g. by hand-held optical fibres, is required.

An alternative method of bimanual vitreous surgery was proposed by Schmidt et al. ("Bimanuelle Membranextraktion bei schwerer proliferativer diabetischer Vitreoretinopathie mit permanenter Endoillumination", Spektrum Augenheilkd. 2003, 17, 177-180). In this, a fourth incision is made through which a light probe is introduced.

For wide angle observation during vitreous surgery, lenses are generally arranged between the operating microscope and the patient's cornea. Apart from so-called corneal contact lenses, the positioning of which is carried out by assistants or by using a retaining ring placed directly on the cornea, wide-angle attachments for operating microscopes are also used.

In order to achieve a sufficient wide-angle view, as a rule aspherical lenses are used in both cases, which produce a reversed, upside down image. The image reversal is acceptable during diagnosis. However, during eye operations the reversal of the image leads to coordination problems, even with experienced surgeons, while the reversed stereopsis is an additional aggravating factor.

Therefore, for the fields of use described, the use of devices for reversing and righting images is known and is described for example in DE 36 15 842 A1, DE 3826069 A1, DE 200 21 955 U1 and WO 91/15150 A1. However, the additional components should not appreciably increase the height of the microscope as the surgeon has to carry out the operation and look through the microscope at the same time. The distance between the eyepiece of the microscope and the patient's eye thus cannot be increased at will.

Moreover, the device for reversing and righting the image should also be capable of being pivoted into the optical path of the microscope as quickly as possible so that it is possible to operate both in the front section of the eye and at the back of the eye without having to change the microscope. It is therefore expedient to use different prism systems (generally with Porro prisms) as disclosed in the above-mentioned DE 200 21 955 U1, which are arranged at the microscope end of the wide-angle lens used.

WO 91/15150 discloses a prism arrangement in which a prism is arranged to be movable in order to lengthen or shorten the observation beam path. This makes it possible to maintain the focus of the microscope even with non-emmetropic eyes when the wide-angle device with its associated prism arrangement for righting the image is pivoted outwards or inwards.

However, the systems proposed still require the insertion of an optical fibre into the eye. As already mentioned, however, it is desirable to reduce such incisions as much as possible.

Furthermore, DE 10 2009 058 792 B3, which was a prior application with respect to the filing date or priority date of the present application in Germany but was published later, relates to an optical observation device for observing an eye. This optical observation device comprises a microscope for observing the front section of the eye and a visualising system that can be pivoted in front of the microscope for observing the retina of the eye. The microscope and the visualising device are used exclusively, i.e. when viewing the front part of the eye the visualising device is pivoted out of the beam path of the microscope, whereas when observing the retina of the eye the attachment module is pivoted in, the observation of the retina then taking place by means of the visualising device which has at least one digital camera, the data from which are supplied to a reflecting or superimposing device of the microscope. The image of the retina can be made visible through the eyepiece of the microscope by means of a display of the reflecting device and corresponding optics and beam splitters. The solution proposed here is complicated as the visualising device itself constitutes a kind of microscope and a reflecting device has to be provided to render the data of the visualising device visible on the microscope. Moreover, the proposed visualising device is not a wide-angle device in the sense of the present application.

From DE 10 2006 038 911 A1, an ophthalmoscopic attachment module is known for attachment to an operating microscope for observing the back of a patient's eye. The background to the solution proposed in this specification is the avoidance of disruptive light reflections emanating from the illuminating light, reflected on the ophthalmoscopic magnifying lens of the attachment module. Therefore, this publication proposes various solutions for guiding light from the microscope illumination past the ophthalmoscopic magnifying lens towards and into the patient's eye that is to be examined. In another embodiment the attachment module has its own light source with illuminating optics. Illuminating light produced there is guided via reflective surfaces past the ophthalmoscopic magnifying lens into the patient's eye. The attachment module proposed therein is, once again, not a wide-angle device in the sense of the present application.

The objective of the present invention is therefore to provide a possible illumination which allows bimanual ophthalmological operations, particularly vitrectomies, without the need for the insertion of a cannula with optical fibre into the patient's eye, and by means of which at least the object field perceived by the observer is fully illuminated at the same time.

SUMMARY OF THE INVENTION

Against this background the invention proposes an operating microscope system for ophthalmology, particularly vitrectomy, as well as an illuminating unit and a wide-angle device for an operating microscope system of this kind, having the features described herein.

The present invention starts from an operating microscope system for ophthalmology, comprising an operating microscope with its own microscope illumination for the magnified imaging of an illuminated object area and a wide-angle device arranged on the objective side of the operating microscope and in front of the latter. The wide-angle device comprises a wide-angle lens arranged on the object side of the wide-angle device and a prism arrangement for righting the image, arranged on the microscope side of the wide-angle lens. Also arranged in the wide-angle device is an illuminating unit by means of which illuminating light produced there is passed through the wide-angle lens onto an object arranged in front of the wide-angle lens. In particular, this enables the illuminating light of the wide-angle device to be shone onto and into a patient's eye as object.

To avoid incisions, so-called fibre-optic-free intravitreal surgical systems are known from the prior art, as described for example by Horiguchi et al. ("New System for Fiberoptic-Free Bimanual Vitreous Surgery", Arch. Ophthalmol. 2002, 120, 491). The light source already provided in the operating microscope is used here as illuminating means. The illuminating light is directed into the observation beam path and shone through the wide-angle lens onto the object under examination. The amount of light shone in is, however, insufficient in many cases, particularly in micro-surgical operations. In addition, annoying reflections may be formed.

The measures proposed provide, by contrast, a controlled, adjustable and effective illuminating light adapted to the particular operating requirements, which emanates from an additional illuminating unit with light source which is to be specially provided (in addition to the normal microscope illumination), thus making it possible at the same time to reduce unwanted incisions into the eye to a minimum.

The effective trauma to the patient's eye is greatly reduced by the fact that, within the scope of the invention, thinner cannulas (e.g. 25 gauge, i.e. less than 0.5 mm) without an optical fibre can advantageously be used within the scope of the invention. These cannulas can be seamlessly inserted and removed through small incisions.

When the system according to the invention is used, there is theoretically no further need for a surgeon to hold an optical fibre manually. Thus the handling of the instruments during bimanual vitrectomy is significantly simplified. Apart from the very much simpler handling of the instruments, there are cost advantages, as fibre optic probes and the like are no longer needed. With the large number of instruments conventionally used in eye surgery, confusion may occur in some unfortunate cases as a result of the cables, optical fibres, control devices and the like located on the operating table, thus hindering the surgical work. Thanks to the device proposed according to the invention the majority of these components are no longer required, which means that corresponding operations are made clearer and simpler.

It is particularly advantageous within the scope of the present invention to use an illuminating unit for the wide-angle device which comprises a beam splitter in addition to a light source. By the use of a beam splitter the light emanating from the light source can very easily be directed into the beam path of a corresponding operating microscope, for example into the beam path of the wide-angle device.

Advantageously, the beam splitter is embodied as a semi-transparent minor, as known from the prior art and available in high quality and with defined characteristics.

It is particularly advantageous to embody one of the prism surfaces of the prism arrangement for righting the image as a semitransparent minor or as a semitransparent prism surface of the wide-angle device so that as a result the light emanating from the light source can be directed particularly effectively into a prism that deflects the observation beam path. The semitransparent reflective prism surface may be produced for example by vapour deposition of metal.

In a beam splitter or minor of this kind, the ratio of reflection to transmission has a value of 60:40 to 90:10 and the values 80:20 or 90:10 are particularly suitable. The higher the proportion of reflection, the more light travels from the object to the viewer (surgeon).

An illuminating unit advantageously comprises a light source and a condenser and/or diaphragm arrangement. By using a condenser and/or diaphragm arrangement the quantity of light and/or the focusing of the illuminating light provided by the light source can be adjusted in a defined manner, so that at any time the quantity of light required within the scope of the operation being undertaken is available in sufficient quantities and in the right place. Moreover, this makes it possible to implement particular lighting techniques if desired.

Advantageously, light emitting semiconductor elements such as LEDs or OLEDs ("Organic LED", thin-film illuminating component comprising organic semiconductor materials) or halogen lamps may be used as the light source, while LEDs in particular are characterised by a particularly high light yield over a small space and with very little heat given off. For particular lighting techniques, special lamps with a defined light spectrum or specific light temperature may advantageously be used.

Advantageously, the wide-angle device and/or the illuminating unit is equipped with at least one light trap, at least one light labyrinth or at least one polarization and/or absorption filter. As a result, light from scattered light sources existing within the wide-angle system can be at least partially suppressed. Scattered light sources of this kind may occur anywhere where there is a transition between media of different refractive indices, i.e. for example on lens and/or prism surfaces. Within the scope of the device according to the invention this is the case particularly at the light source, a condenser lens associated with the illuminating unit and/or the beam splitter. By use of corresponding polarisation and/or absorption filters, scattered light with different wavelengths or polarisation may be filtered from the light used for observing the object. Polarisation filters should also include λ/4 plates, circular polarising filters and birefringent optical components which may be used to prevent light scatter.

It is regarded as particularly advantageous to configure the illuminating unit at least partly as an integral component of the wide-angle device. As a result a very small arrangement can be produced, the size of which does not exceed, or only slightly exceeds, that of a conventional prism arrangement for righting an image or a wide-angle device. On the one hand the entire illuminating unit can be integrated in a corresponding assembly. This then only has to be connected to a source of current. However, it is also possible to provide an entry point for the coupling of an optical fibre in a wide-angle device, so that externally produced light can be directed in.

As already mentioned, the proposed operating microscope is particularly suitable for use in ophthalmology, particularly vitrectomy.

With regard to the illuminating unit also proposed according to the invention and the corresponding wide-angle device, reference is made specifically to the features and advantages described above.

Usually, the wide-angle devices can be pivoted into the observation beam path of the operating microscope as necessary. To enable microscopic observation even without a wide-angle device, the operating microscope must have its own microscope illumination (microscope illumination system with microscope light source). When the wide-angle device is pivoted inwards, it may be advantageous to switch off the microscope illuminating unit and to work only with the illuminating unit of the wide-angle device. An automatic device may ensure that when the wide-angle device is pivoted inwards the microscope illumination is switched off and, in parallel, the illuminating unit of the wide angle device is switched on. At the same time other parameters on the operating microscope may be adjusted to suit optimum wide-angle observation.

Further advantages and embodiments of the invention will become apparent from the description and the accompanying drawings.

It will be understood that the features mentioned above and those still to be described hereinafter may be used not only in the particular combination specified but also in other combinations or on their own, without departing from the scope of the present invention.

BRIEF DESCRIPTION OF THE DRAWINGS

The invention is schematically illustrated by embodiments by way of example shown in the drawings and is described in detail hereinafter with reference to the drawings, in which.

In the Figures that follow, elements that are identical or have identical functions have been given identical reference numerals. In the interests of clarity the explanations have not been repeated.

DEFINITIONS OF TERMS

Figure 1:
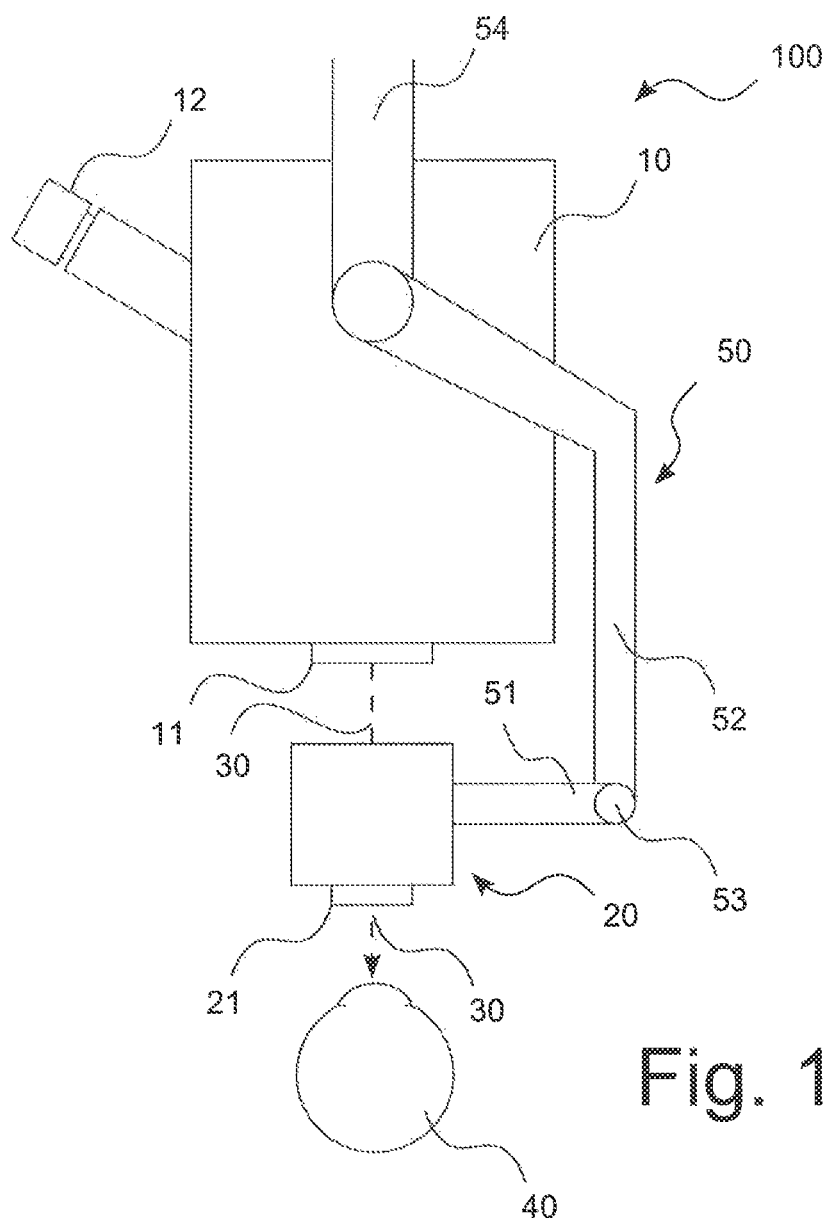
FIG. 1 shows an operating microscope with a wide-angle device according to the prior art.

FIG. 1 shows an operating microscope system, generally designated 100, having an operating microscope 10 with which is associated a wide-angle device 20. The operating microscope 10 is arranged for stereoscopic viewing and has an objective 11 and a viewer with eyepieces 12.

Figure 3:
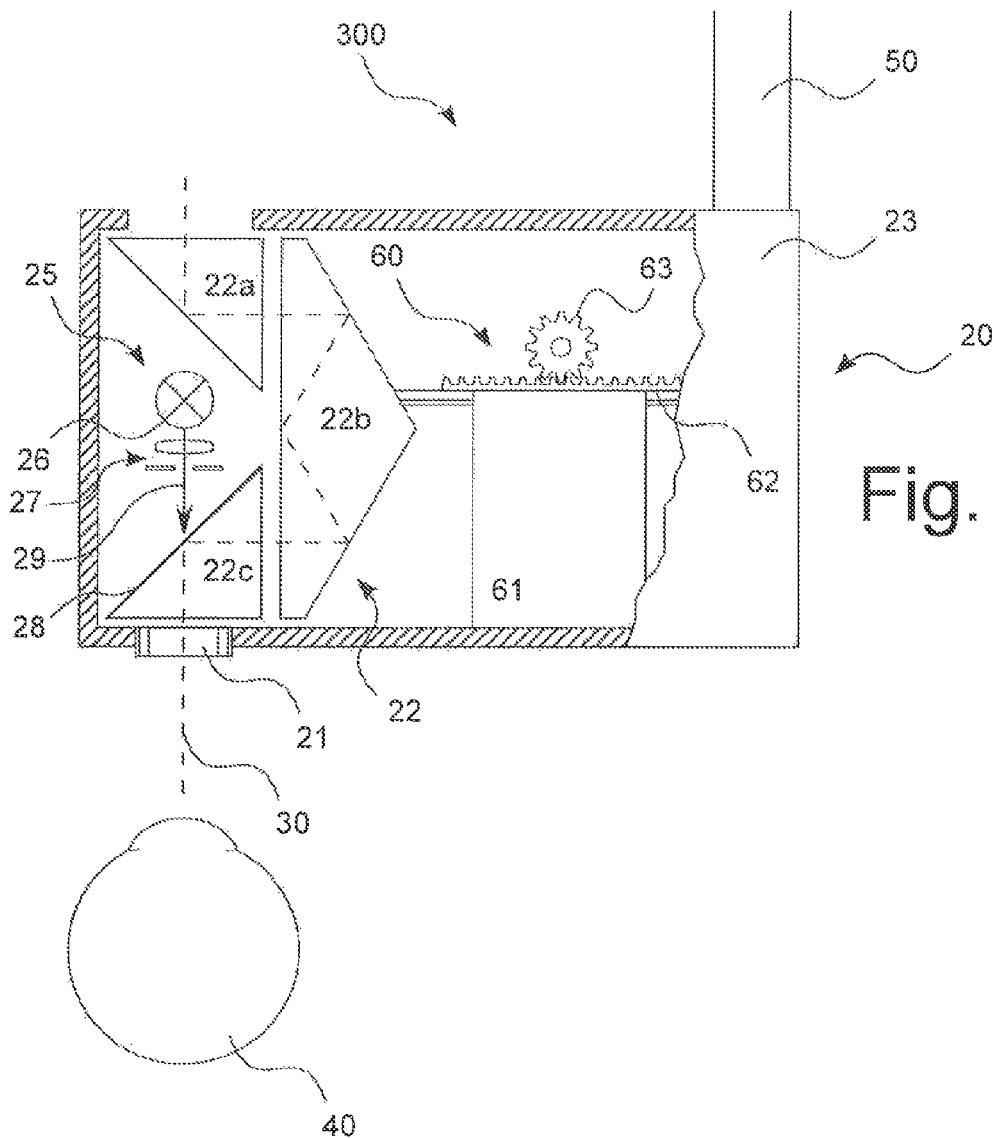
FIG. 3 shows a wide-angle device according to a preferred embodiment of the invention.
Figure 4:
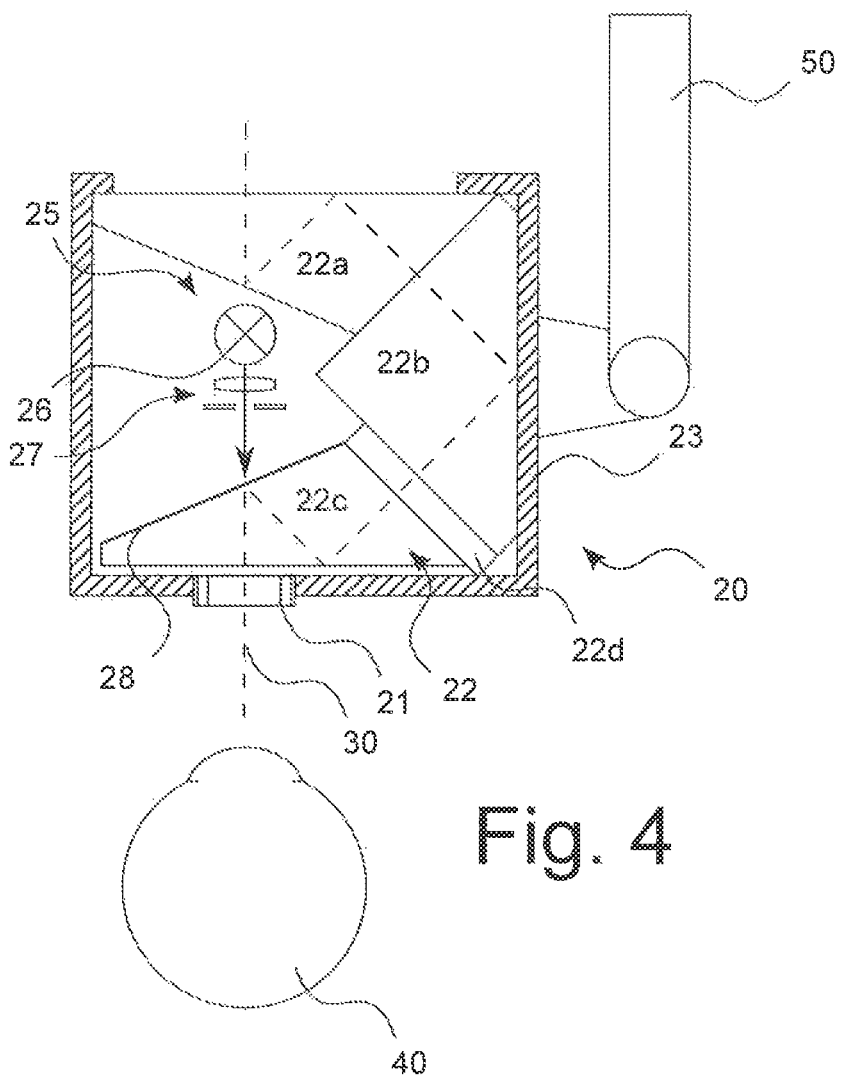
FIG. 4 shows a wide-angle device according to a preferred embodiment of the invention.

On the objective side of the operating microscope 10 is provided the wide-angle device 20 which is shown in more detail in FIGS. 3 and 4. The wide-angle device 20 comprises a wide-angle lens 21 arranged on the object side. On the microscope side of the wide-angle lens 21 is provided a prism arrangement (not shown here).

As indicated by the dashed arrow, an observation beam path 30 passes through the objective 11 and the wide-angle device 20 with the wide-angle lens 21 and is directed to a patient's eye 40. The operating microscope 10 and the wide-angle device 20 are held on a support arm system 50. The support arm system 50 may be attached by means of a holder 50 to a stand (not shown) or to a ceiling, for example. The wide-angle device 20 is attached to a holder 52 by means of an additional support arm 51 and is preferably horizontally and vertically pivotable about a pivot point 53. Therefore, the wide-angle device 20 as a whole can be pivoted out of the observation beam path (horizontally and/or vertically).

Figure 2:
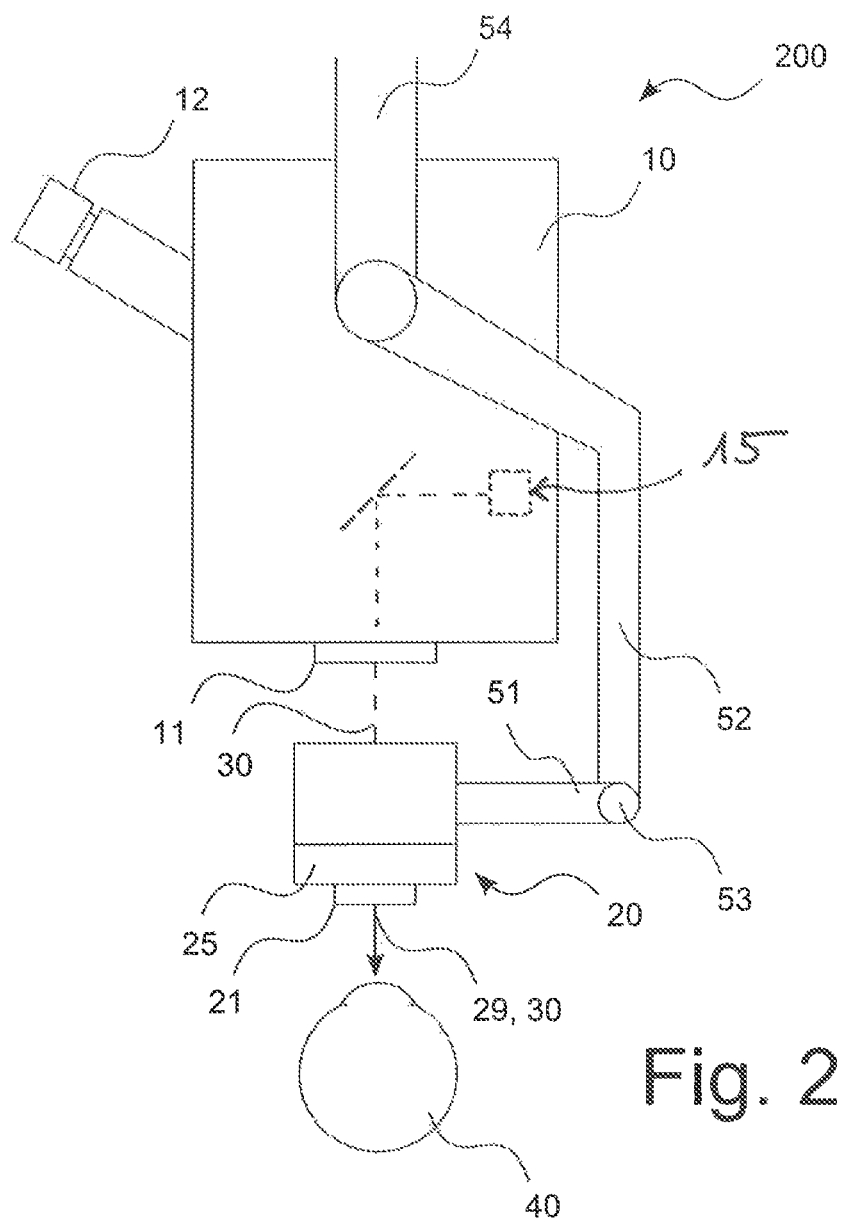
FIG. 2 shows an operating microscope with a wide-angle device according to a preferred embodiment of the invention.

FIG. 2 shows the operating microscope system with the operating microscope 10 of FIG. 1 with a wide-angle device 20, this operating microscope system being generally designated 200. In contrast to FIG. 1, as explained in more detail hereinafter, an illuminating unit 25 integrated in the wide-angle device 20 and shown purely schematically here is provided, by means of which illuminating light 29 can be directed through the wide-angle lens 21 onto or into the patient's eye 40. As can be seen from FIG. 2, the operating microscope system 200 in FIG. 2 can be equipped with the illuminating function without any appreciable change to its size. The microscope illumination shown schematically and by dashed lines is generally designated 15.

FIG. 3 shows, generally designated 300, a detailed view of a wide-angle device 20 with an illuminating unit 25 according to a particularly preferred embodiment. On the object side of the wide-angle device 20 is schematically shown a wide-angle lens 21, which may be, for example, a 40D aspherical lens. On the microscope side of the wide-angle lens 21 is provided a prism arrangement 22 for righting the laterally reversed image of the patient's eye 40 provided by the wide-angle lens 21.

The prism arrangement 22 has three prisms 22a, 22b, 22c, through which the observation beam path 30 is deflected numerous times and can finally be observed as a correct image by means of the operating microscope (not shown). The elements of the wide-angle device 20 are accommodated in a housing 23 which is shown partly cut away. The wide-angle device 20 has an integrated illuminating unit 25 which comprises a light source 26, e.g. a LED or a halogen lamp, and a condenser and/or diaphragm arrangement 27. An illuminating light 29 thus produced is directed into the beam path through a beam splitter 28, which in this case is embodied as a semitransparent prism surface of the prism 22c, and passed through the wide-angle lens 21 and into the patient's eye 40. Although this is not shown in FIG. 3, corresponding connecting means, for example current supply means, and/or cooling means such as ventilators or cooling ribs, to eliminate excess heat, may be provided. Instead of a light source 26 it may also be possible to direct light from a cold light source through a optical fibre into the wide-angle device 20 at a suitable point. In addition to the light source 26 of the illuminating unit 25 of the wide-angle device 20, the operating microscope 10 has its own microscope illumination 15, which may be of conventional design. It is advantageous to switch off this microscope illumination 15 (shown in FIG. 2) when the wide-angle device 20 is pivoted into the observation beam path 30 of the operating microscope 10 (cf. FIG. 2). Not shown in detail is a carrier system 50, which may be of similar construction to that described above.

In the embodiment shown, in order to lengthen and/or shorten the observation beam path 30, an adjusting device 60 is provided for moving the prism 22b of the prism arrangement 22, having a rack 62 and an adjustable pinion 63 (adjusting means associated therewith are not shown). By adjusting the pinion 63 the rack 62 is moved along and the prism 22b is moved so that, as explained previously, long-sighted and/or short-sighted eyes can be examined or operated on with the wide-angle device 20 pivoted in and out, without the need to change the focus of the microscope.

FIG. 4 shows a wide-angle device with an illuminating unit according to another embodiment of the invention, generally designed 400. The wide-angle device in this embodiment essentially differs from the one in FIG. 3 by the use of a different type of prism. Once again, an observation beam path 30 is deflected multiple times and thus righted by the prisms or optical elements 22a to 22d that are provided. Light emanating from an illuminating unit 25 is directed into the beam path and passes into the patient's eye 40.

As is clear particularly from FIGS. 3 and 4 explained hereinbefore, the present invention is not restricted to special types of prism; rather, all kinds of prisms may be used that allow the correction of an optical image and that allow the directing of an illuminating beam path particularly through semitransparent prism surfaces. Lens and/or mirror arrangements with corresponding functions may also be used.

The invention is not to be limited to the specific embodiments disclosed, and modifications and other embodiments are intended to be included within the scope of the invention.

LIST OF REFERENCE CHARACTERS

10 Operating microscope
11 Objective
12 Eyepieces
Microscope illumination
20 Wide-angle device
21 Wide-angle lens
22 Prism arrangement
22a, 22b, 22c Prism
22d Optical element
23 Housing
25 Illuminating unit
26 Light source
27 Condenser and/or diaphragm arrangement
28 Beam splitter
29 Illuminating light
30 Observation beam path
40 Object, patient's eye
50 Support arm system
51 Support arm
52 Holder
53 Pivot point
54 Holder
60 Adjusting device
61 Support
62 Rack
63 Pinion
100, 200 Operating microscope system
300, 400 Wide-angle device with illuminating unit

What is claimed is:

1. An operating microscope system (200) for ophthalmology, comprising:
an operating microscope (10) comprising a microscope illumination (15) and a wide-angle device (20) arranged on the objective side in front of the operating microscope (10), the wide-angle device (20) having a wide-angle lens (21) arranged on the object side of the wide-angle device (20); and
a prism arrangement (22) for righting the image arranged on the microscope side of the wide-angle lens (21);
wherein the wide-angle device (20) comprises an illuminating unit (25) arranged to illuminate an object (40) through the wide-angle lens (21) by an illuminating light (29), the object being arranged in front of the wide-angle lens (21).

2. The operating microscope system (200) according to claim 1, wherein the wide-angle device (20) comprises a beam splitter (28) by which the illuminating light (29) can be directed into an observation beam path (30) of the operating microscope (200).

3. The operating microscope system (200) according to claim 2, wherein the beam splitter is embodied as a semitransparent mirror (28).

4. The operating microscope system (200) according to claim 3, wherein the semitransparent mirror (28) is embodied as a semitransparent prism surface of the prism arrangement (22) for righting the image.

5. The operating microscope system (200) according to claim 3, wherein the reflection/transmission ratio of the semitransparent mirror (28) is 60:40 to 90:10.

6. The operating microscope system (200) according to claim 2, wherein the illuminating unit (25) comprises a light source (26) and a condenser and/or diaphragm arrangement (27).

7. The operating microscope system (200) according to claim 6, wherein the light source (26) comprises a light emitting semiconductor element and/or a halogen lamp.

8. The operating microscope system (200) according to claim 1, wherein the wide-angle device (20) and/or the illuminating unit (25) comprise(s) a light trap and/or a light labyrinth.

9. The operating microscope system (200) according to claim 1, wherein the wide-angle device (20) and/or the illuminating unit (25) comprise(s) a polarisation and/or absorption filter.

10. The operating microscope system (200) according to claim 1, wherein the illuminating unit (25) is at least partially embodied as an integral component of the wide-angle device (20).

11. The operating microscope system (200) according to claim 1, adapted for use in vitrectomy.

12. An illuminating unit (25) for an operating microscope system (200) according to claim 1, which is embodied as part of a wide-angle device (20) arranged in front of an operating microscope (10) of the operating microscope system (200).

13. A wide angle device (20) for an operating microscope system (200) according to claim 1, which is arranged in front of an operating microscope (10) of the operating microscope system (200) and comprises an illuminating unit (25) according to claim 12.

* * * * *